(12) United States Patent
Ishii et al.

(10) Patent No.: US 10,023,529 B2
(45) Date of Patent: Jul. 17, 2018

(54) APPARATUS FOR REMOVING CATALYST SURFACE SUBSTANCES

(75) Inventors: Yusuke Ishii, Tokyo (JP); Yasuaki Furuya, Tokyo (JP); Toshihiko Fukuzono, Tokyo (JP)

(73) Assignee: ASAKI KASEI CHEMICALS CORPORATION, Tokyo (JP)

( * ) Notice: Subject to any disclaimer, the term of this patent is extended or adjusted under 35 U.S.C. 154(b) by 143 days.

(21) Appl. No.: 13/634,479

(22) PCT Filed: Apr. 26, 2011

(86) PCT No.: PCT/JP2011/060157
§ 371 (c)(1),
(2), (4) Date: Sep. 12, 2012

(87) PCT Pub. No.: WO2011/136217
PCT Pub. Date: Nov. 3, 2011

(65) Prior Publication Data
US 2013/0041172 A1 Feb. 14, 2013

(30) Foreign Application Priority Data

Apr. 30, 2010 (JP) .................. 2010-105511

(51) Int. Cl.
*B01J 8/18* (2006.01)
*B01J 8/24* (2006.01)
(Continued)

(52) U.S. Cl.
CPC .......... *C07C 253/24* (2013.01); *B01J 8/1818* (2013.01); *B01J 8/1863* (2013.01); *B01J 8/388* (2013.01);
(Continued)

(58) Field of Classification Search
None
See application file for complete search history.

(56) References Cited

U.S. PATENT DOCUMENTS 2,421,212 A * 5/1947 Medlin ................... 208/152
3,259,998 A * 7/1966 LeClere et al. ........... 34/585
(Continued)

FOREIGN PATENT DOCUMENTS

CN 1188105 A 7/1998
FR 1058043 A * 3/1954
(Continued)

OTHER PUBLICATIONS

Machine translation of FR 1058043 A (Mar. 1954).*
(Continued)

*Primary Examiner* — Jennifer A Leung
(74) *Attorney, Agent, or Firm* — Finnegan, Henderson, Farabow, Garrett & Dunner, LLP

(57) ABSTRACT

An apparatus for efficiently removing the exuded substance and/or the attached substance on the surface of a catalyst (catalyst surface substance) from the catalyst is provided. The apparatus comprising a main body, the apparatus for removing a catalyst surface substance present on a surface of a catalyst from the catalyst by bringing a gas flow into contact with the catalyst housed in the main body, wherein a gas flow length in a flow direction of the gas flow is 55 mm or more, and an average flow velocity of the gas flow is 80 m/s or more and 500 m/s or less in terms of a linear velocity at 15° C. and 1 atm.

8 Claims, 6 Drawing Sheets

(51) Int. Cl.
- *B01J 8/44* (2006.01)
- *C07C 253/24* (2006.01)
- *B01J 8/38* (2006.01)
- *B01J 38/04* (2006.01)
- *B01J 23/00* (2006.01)
- *B01J 23/28* (2006.01)
- *B01J 37/00* (2006.01)

(52) U.S. Cl.
CPC .............. B01J 8/44 (2013.01); B01J 38/04 (2013.01); *B01J 23/002* (2013.01); *B01J 23/28* (2013.01); *B01J 37/0045* (2013.01); *B01J 2208/0092* (2013.01); *B01J 2208/00902* (2013.01); *B01J 2208/00911* (2013.01); *B01J 2523/00* (2013.01); *Y02P 20/52* (2015.11); *Y02P 20/584* (2015.11)

(56) References Cited

U.S. PATENT DOCUMENTS

| | | | | |
|---|---|---|---|---|
| 4,372,228 A | * | 2/1983 | Korenberg | 110/347 |
| 4,392,943 A | * | 7/1983 | Euzen | B01J 8/003 208/152 |
| 5,124,291 A | | 6/1992 | Bremer et al. | |
| 5,158,919 A | * | 10/1992 | Haddad et al. | 502/44 |
| 5,854,161 A | | 12/1998 | Ichiki et al. | |
| 5,914,424 A | | 6/1999 | Nakamura et al. | |

FOREIGN PATENT DOCUMENTS

| | | | | |
|---|---|---|---|---|
| GB | 577581 A | * | 5/1946 | B01J 10/00 |
| GB | 1265770 A | * | 3/1972 | |
| JP | 08-294635 | | 11/1996 | |
| JP | 08-318168 | | 12/1996 | |
| JP | 09-038507 A | | 2/1997 | |
| JP | 2000-144151 A | | 5/2000 | |
| JP | 2000-202241 | | 7/2000 | |
| JP | 2007-216212 | | 8/2007 | |

OTHER PUBLICATIONS

English-Language Translation of International Search Report from the Japanese Patent Office for International Application No. PCT/JP2011/060157, dated Aug. 16, 2011.

Chinese Patent Office, Office Action dated Jan. 6, 2014 for Chinese Application No. 201180021918.9.

Japan Patent Office, Office Action dated Feb. 24, 2014 for Japanese Application No. 2012-512855 (2 pages).

* cited by examiner

APPARATUS FOR REMOVING CATALYST SURFACE SUBSTANCES

BACKGROUND OF THE INVENTION

Field of the Invention

The present invention relates to an apparatus for removing the catalyst surface substances from a catalyst.

Description of the Related Art

The fluidized bed reaction is applied to a wide variety of reactions because the fluidized bed reaction has such a satisfactory handleability that the catalyst involved can be extracted and replenished even during operation and moreover, the temperature gradient inside the reactor is smaller and the heat removal efficiency is higher as compared to the fixed bed. For example, an intended nitrile has been produced by ammoxidation of an alkene with a fluidized bed reactor, and for the purpose of making the fluidized bed reaction efficiently proceed, various reaction conditions in the fluidized bed reaction have also been investigated.

On the other hand, the physical properties known to be required for the catalyst in the fluidized bed reaction include the high fluidity and the high abrasion resistance. Japanese Patent Laid-Open No. 2007-216212 describes the fact that when exuded substances and/or attached substances are present on the surface of a catalyst, the fluidity is impaired, and also the fact that when the exuded substances and/or the attached substances are present in an amount of 2 wt % or more based on the mass of the catalyst, the fluidity is degraded and the reaction is not stabilized.

SUMMARY OF THE INVENTION

As described in Japanese Patent Laid-Open No. 2007-216212, when the exuded substances and/or the attached substances are present on the surface of a catalyst, the fluidity of the catalyst is degraded, and hence it is preferable to remove these substances from the surface of the catalyst, in advance of the fluidized bed reaction. When the exuded substances and/or the attached substances on the surface of a catalyst are removed according to the method described in Japanese Patent Laid-Open No. 2007-216212, such a small amount of a catalyst as the level of the amount used in researches can be processed without problems; however, the method according to Japanese Patent Laid-Open No. 2007-216212 is inefficient for the purpose of processing catalysts in industrially used amounts.

In view of the above-described circumstances, an object of the present invention is to provide an apparatus for efficiently removing the exuded substances and/or the attached substances (catalyst surface substances) on the surface of a catalyst from the catalyst.

The present inventors made a diligent study in order to solve the above-described problems, and consequently have completed the present invention by discovering that the above-described problems can be solved by using an apparatus bringing, into contact with a catalyst, a gas flow in which the gas flow length in the flow direction of the gas flow and the average flow velocity are adjusted to fall within specified ranges, respectively.

Specifically, the present invention is as follows.

[1]

An apparatus comprising a main body, the apparatus for removing a catalyst surface substance present on a surface of a catalyst from the catalyst by bringing a gas flow into contact with the catalyst housed inside the main body, wherein a gas flow length in a flow direction of the gas flow is 55 mm or more, and an average flow velocity of the gas flow is 80 m/s or more and 500 m/s or less in terms of a linear velocity at 15° C. and 1 atm.

[2]

The apparatus according to [1], the apparatus further comprising a passage orifice of the gas flow inside the main body, wherein a converted energy value per an unit mass of the catalyst $u^2 \times V \times K/M$ derived from a flow velocity u (m/s) of the gas flow at the passage orifice, a volume V (m³) formed by the gas flow having passed through the passage orifice, the number K of the passage orifices inside the main body, and a mass M (kg) of the catalyst housed inside the main body satisfies a following formula (1):

$$14 < u^2 \times V \times K/M < 100 \tag{1}$$

[3]

The apparatus according to [1] or [2], comprising: a collection device for collecting the catalyst, placed in an upper portion of the main body; and a return device for returning the catalyst, connected to the collection device, wherein the return device is placed so as for a lower end thereof to be brought into contact with the gas flow, and a fraction of the catalyst, brought into contact with the gas flow inside the main body is collected by the collection device and returned inside the main body by the return device.

[4]

The apparatus according to [3], further comprising a device for capturing the catalyst surface substance removed from the catalyst.

[5]

The apparatus according to any one of [1] to [4], wherein the collection device includes a separation device for separating the catalyst and the catalyst surface substance from each other by a centrifugal force.

[6]

The apparatus according to any one of [1] to [5], wherein the apparatus is designed so as for the gas flow to be ejected in a plurality of directions.

[7]

A method for removing a catalyst surface substance from a catalyst by bringing a gas flow into contact with the catalyst, the method including a step of bringing a gas flow into contact with the catalyst having the catalyst surface substance, wherein a gas flow length in a flow direction of the gas flow is 55 mm or more, and an average flow velocity of the gas flow is 80 m/s or more and 500 m/s or less in terms of a linear velocity at 15° C. and 1 atm.

[8]

The method according to [7], wherein the catalyst is housed inside the main body comprising a passage orifice of the gas flow, and a converted energy value per an unit mass of the catalyst $u^2 \times V \times K/M$ derived from a flow velocity u (m/s) of the gas flow at the passage orifice, a volume V (m³) formed by the gas flow having passed through the passage orifice, the number K of the passage orifices inside the main body, and a mass M (kg) of the catalyst housed inside the main body satisfies a following formula (1):

$$14 < u^2 \times V \times K/M < 100 \tag{1}$$

[9]

A production method, wherein the catalyst surface substance is removed from the catalyst with the apparatus according to any one of [1] to [6], the catalyst from which the catalyst surface substance have been removed is used, and thus an alkane and/or an alkene is subjected to an oxidation reaction or an ammoxidation reaction to produce a corresponding unsaturated acid or unsaturated nitrile.

According to the present invention, the exuded catalyst surface substances and/or the attached catalyst surface substances on the surface of a catalyst can be efficiently removed from the catalyst.

DETAILED DESCRIPTION OF THE PREFERRED EMBODIMENT

Figure 1:
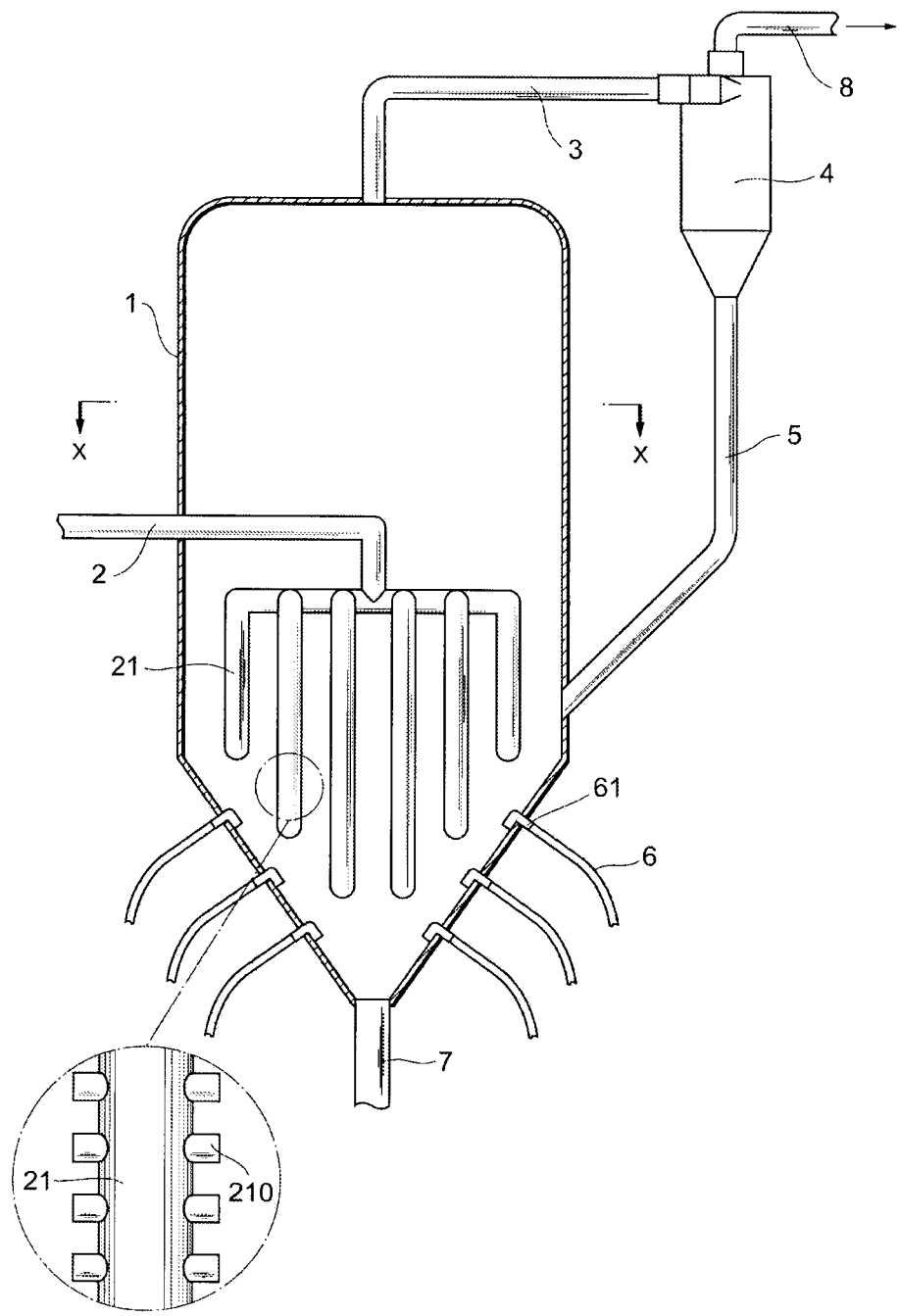
FIG. 1 is a view schematically illustrating an example of an apparatus for removing catalyst surface substances of an embodiment of the present invention.

Hereinafter, the embodiment for carrying out the present invention (hereinafter, referred to as "the present embodiment") is described in detail. The present invention is not limited to the following embodiment, and is capable of being carried out as variously modified within the scope of the gist of the present invention. The embodiment is described, where necessary, with reference to the accompanying drawings; in this connection, it is to be noted that the drawings are presented schematically. Accordingly, the specific dimensions and the like are to be assessed in light of the following description. Needless to say, as far as the dimensional relations and the proportional relations between the drawings and the like are concerned, some portions included in the drawings may deviate from what are accurate or correct. The descriptions of the members common between some of the drawings are omitted as the case may be.

The apparatus for removing a catalyst surface substance of the present embodiment includes a main body, and removes the catalyst surface substance present on the surface of a catalyst from the catalyst by bringing a gas flow into contact with the catalyst housed in the main body, wherein a gas flow length in the flow direction of the gas flow is 55 mm or more, and an average flow velocity of the gas flow is 80 m/s or more and 500 m/s or less in terms of a linear velocity at 15° C. and 1 atm.

The "catalyst surface substance" as referred to in the present embodiment represents the exuded substances and/or the attached substances on the surface of a catalyst, more specifically, the substances protruding from the surface of a catalyst or the substances attached on the surface of a catalyst. In the case of a fluidized bed catalyst composed of an oxide or oxides, the catalyst surface substances are mostly protruding oxide crystals and other impurities. In particular, in the case of an oxide catalyst containing a plurality of metals, those oxides different in composition from the crystal that forms most of the catalyst may be formed in a shape and condition as exuded from the main body of the catalyst. In such a case, the catalyst surface substances are frequently formed on the surface of the approximately spherical fluidized bed catalyst (for example, the diameter is 30 to 150 μm) in a plurality of shapes like protrusions (for example, the height is 0.1 μm to 20 μm).

When the catalyst used in a fluidized bed reaction has the catalyst surface substances or when the catalyst surface substances exfoliated from the catalyst and the catalyst are present in an intermingled manner, the fluidity of the catalyst tends to be degraded. The degradation of the fluidity of the catalyst is accompanied by the uneven distribution of the catalyst in the reactor, consequently the heat removal efficiency is decreased, and heat is accumulated to cause abnormal reactions, or depending on the reactions, to possibly promote the decomposition reaction of the targeted product. When the catalyst surface substances are partially defoliated due to the mutual contact of the catalyst particles inside the reactor and discharged from inside the reactor to outside the concerned reaction system, the exfoliated catalyst surface substances are mixed in the subsequent step, and the load on the subsequent step may be increased. Accordingly, it is preferable to avoid the situation such that the catalyst and the catalyst surface substances are present in an intermingled manner in the fluidized bed reactor.

FIG. 1 schematically shows an example of an apparatus for removing catalyst surface substances of the present embodiment. The apparatus shown in FIG. 1 has a main body 1, a gas introduction pipe 2 penetrating through the side wall of the main body 1, and an outlet pipe 3 disposed on the top side of the main body 1 and connected to a cyclone 4.

The main body 1 is approximately cylindrical, and the lower section of the main body 1 has a reverse conical shape. The main body 1 houses a catalyst, and from the viewpoint of efficiently removing the catalyst surface substances, the amount of the housed catalyst is preferably such that the gas introduction opening located at the vertically highest position of the gas introduction pipe 2 in the main body 1 is immersed in the catalyst in a static condition. A large amount of a catalyst may be housed in the main body 1; however, in such a case, it is necessary to consider the separation ability of the separation apparatus such as a cyclone.

Figure 2:
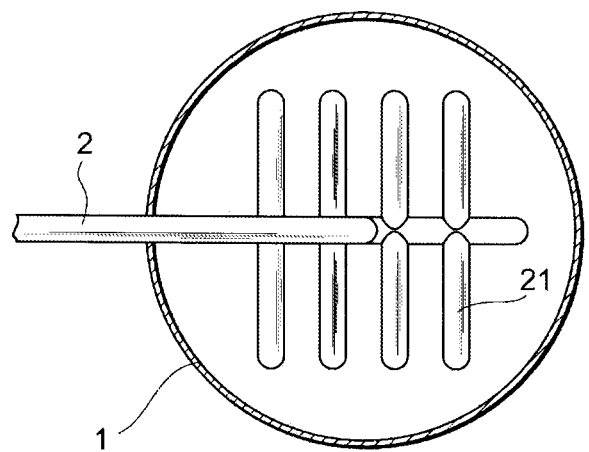
FIG. 2 is a view illustrating the X-X cross section of the apparatus of FIG. 1 for removing catalyst surface substances.

The gas introduction pipe 2 is horizontally introduced at the height approximately half the height of the main body 1, and as shown in FIG. 2, is branched in the vicinity of the center of the main body 1 so as to further form drooping branched chains 21. In the example shown in FIG. 1, a plurality of branched chains 21 of the gas introduction pipe 2 are arranged vertically downward; the direction of the branched chains 21 is not restricted to this, but may be upward, both upward and downward, or horizontal. As shown in a partially enlarged figure of FIG. 1, the individual branched chains 21 each have a plurality of nozzles 210, the gas fed through the gas introduction pipe 2 is ejected from individual nozzles 210. The structure of the branched chain 21 is not limited to the structure having the nozzles 210, may have a plurality of openings 211 in the branched chain 21 as shown in FIG. 3(a), or may have secondary branches 22 perpendicular to the branched chain 21 in such a way that each of the secondary branches 22 may have a plurality of openings 220 as shown in FIG. 3(b). In the conical lower part of the main body, a plurality of lower part gas introduction nozzles 6 are fitted. In the example shown in FIG. 1, the gas introduction nozzles 6 are L-shaped, and are opened obliquely downward after perpendicularly introduced into the main body, and hence the catalyst accumulated in the main body is made to flow downward in the main body 1 by the gas introduced from the nozzles 6. The lower end of the main body 1 is opened to be connected to a second gas introduction pipe 7, and hence the catalyst collected in the lower end by the gas fed from the gas introduction nozzles 6 is made to flow in the main body 1 by the gas fed from the second gas introduction pipe 7. The shape of the gas introduction nozzle end 61 is not limited to an L-shape, and may be of an I-shape or just an opening on the wall without having a nozzle projecting from the inner wall of the main body 1. In the case of the L-shaped nozzle, the nozzles are not required to be opened downward, and may be appropriately set to be opened upward, transversely or in other directions depending on the correlation with the direction of the gas fed from the other second gas introduction pipe 7, the shape of the main body 1 and the like.

One end of an outlet pipe 3 is fixed at the central portion of the upper face of the main body 1, and the other end of the outlet pipe 3 is connected to a cyclone 4. The cyclone 4 separates the catalyst and the catalyst surface substances separated from the catalyst from each other by centrifugal force. Relatively large catalyst particles return from the lower end of the cyclone through a pipe 5 to the main body 1, and on the other hand the catalyst surface substances are light in weight and hence are removed through a discharge line 8 having an opening on the upper face of the cyclone. A filter (not shown) is preferably set at an end of the discharge line 8 so as to capture the discharged catalyst surface substances.

Figure 4:
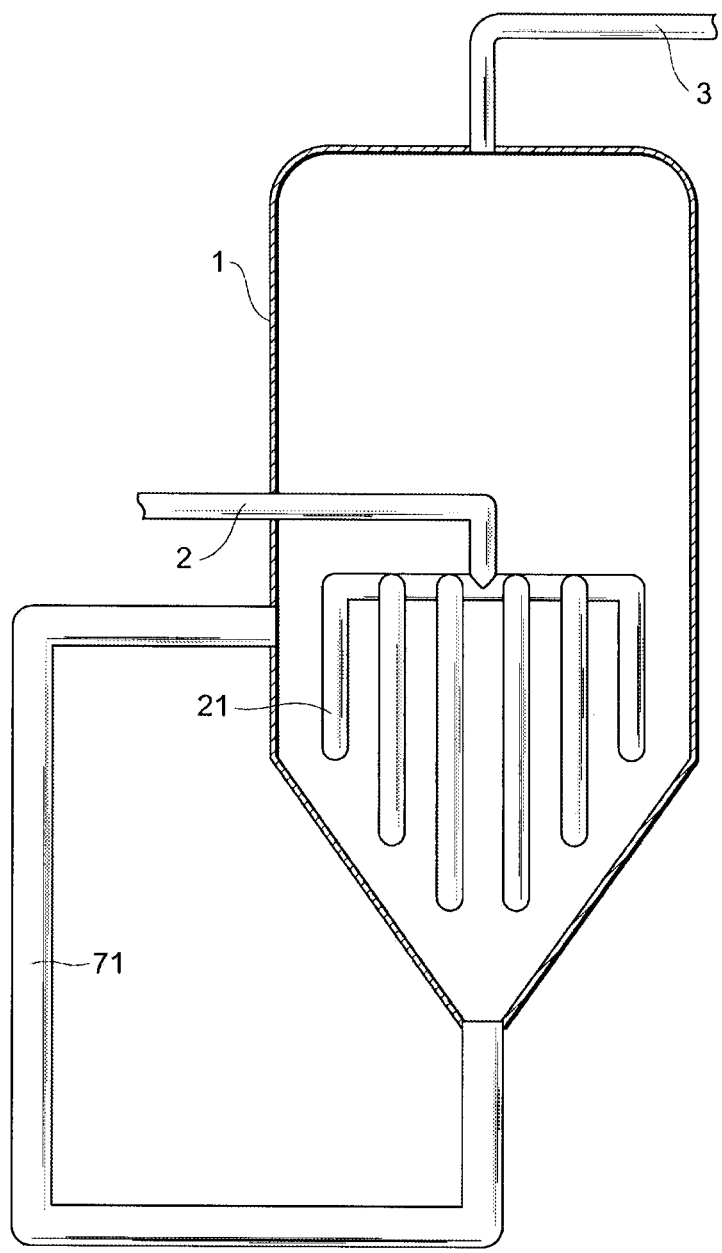
FIG. 4 is a view schematically illustrating an example of an apparatus for removing catalyst surface substances of the embodiment of the present invention.

The apparatus shown in FIG. 4 is the same as the example shown in FIG. 1 except that a catalyst circulation line 71 is provided at the lower end of the main body 1. The other end of the circulation line 71 has an opening on the side of the main body 1, and hence the catalyst flowing into the circulation line 71 is gas-conveyed to be returned to inside the main body 1 by providing a pneumer or the like in the line 71.

Figure 5:
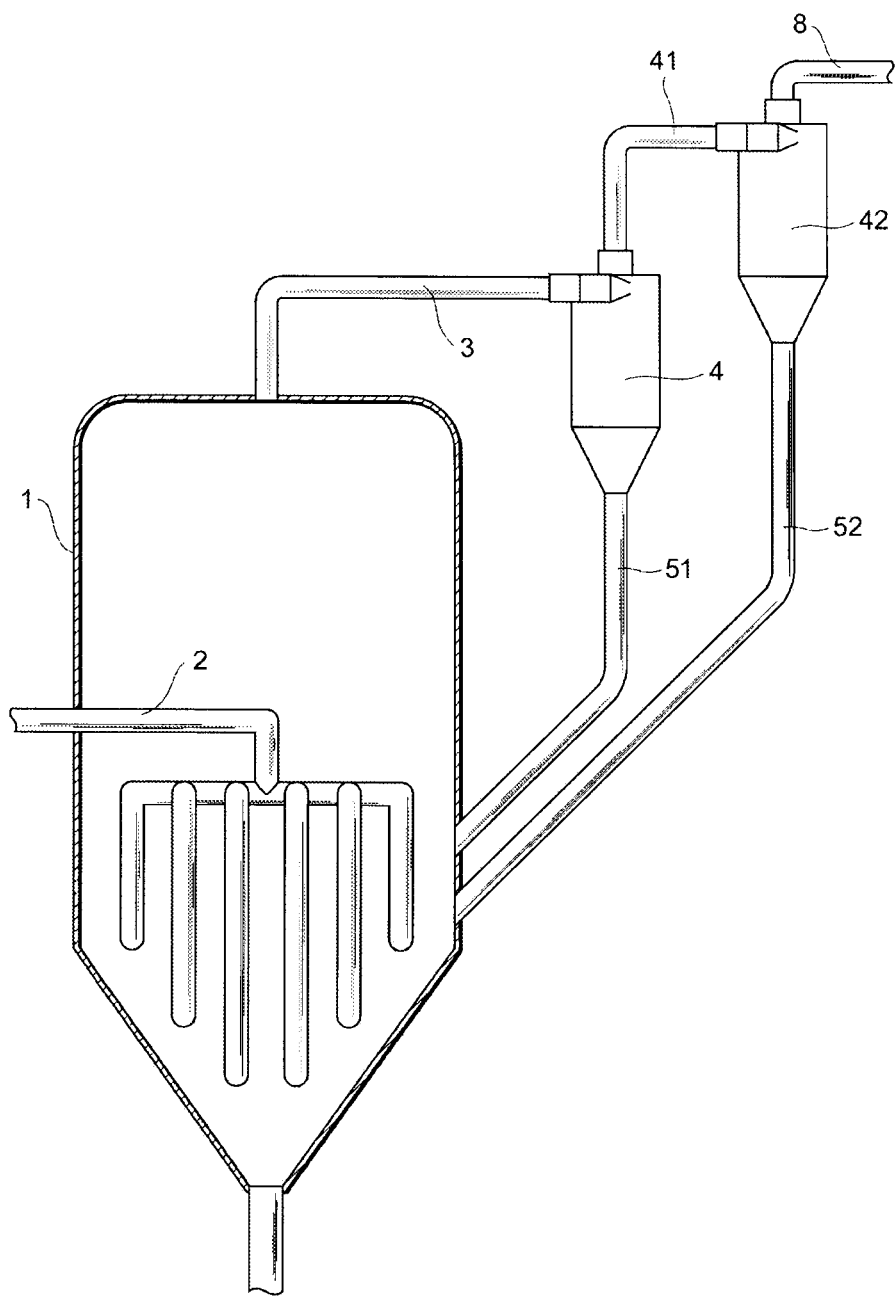
FIG. 5 is a view schematically illustrating an example of an apparatus for removing catalyst surface substances of the embodiment of the present invention.

The apparatus shown in FIG. 5 is the same as the apparatus shown in FIG. 1 except that a second cyclone 42 is connected to the outlet pipe 41 of a first cyclone 4. The return pipes 51, 52 respectively set at the lower ends of the first cyclone 4 and the second cyclone 42 are connected to the side of the main body 1 so as to return the collected catalyst into the main body 1.

Figure 6:
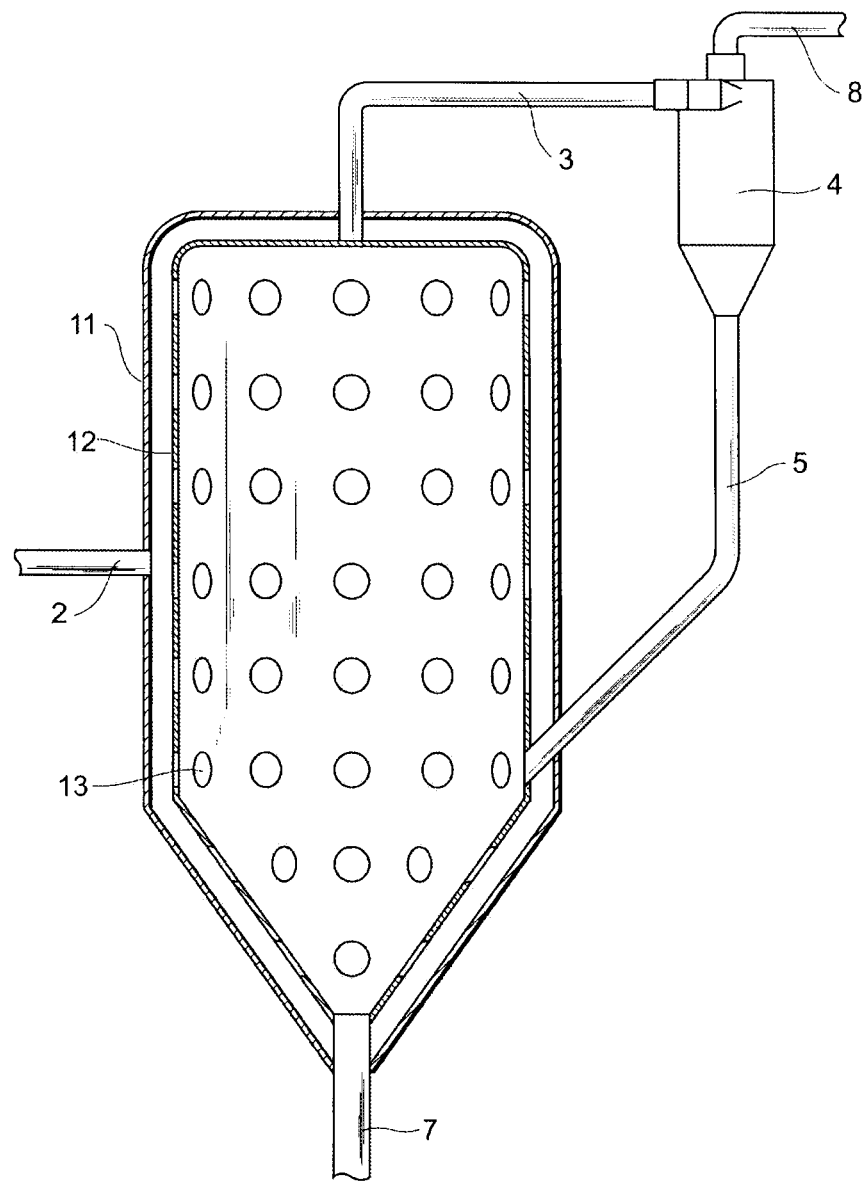
FIG. 6 is a view schematically illustrating an example of an apparatus for removing catalyst surface substances of the embodiment of the present invention.

The apparatus shown in FIG. 6 is nearly the same as the apparatus shown in FIG. 1 except that the main body 1 is of a double structure consisting of an outer pipe 11 and an inner pipe 12 so as to allow gas to be introduced into between the outer pipe 11 and the inner pipe 12 from a gas introduction pipe 2; therefore, only the differences between these apparatuses are described. The inner pipe 12 has a plurality of orifices 13, the gas fed into between the outer pipe 11 and the inner pipe 12 is ejected from the orifices 13 into the interior of the main body 1. The inner pipe 12 has openings to an outlet pipe 3 and a return pipe 5, but the outer pipe 11 is not connected to these openings, and hence the catalyst does not come into between the outer pipe 11 and the inner pipe 12, passes through the outlet pipe 3 to get into a cyclone 4, and is returned from a return pipe 5 into the main body 1. A second gas introduction pipe 7 also has an opening only to the inner pipe 12, and an appropriate amount of gas can be fed from the gas introduction pipe 7 so as to avoid the accumulation of the catalyst at the bottom of the main body 1.

Although in the example of FIG. 6, no gas introduction pipe 2 having a plurality of branch chains 21 are provided, a gas introduction pipe 2 having a plurality of branch chains 21 as shown in FIG. 1 may also be provided even in the case where an apparatus has a double structure main body 1.

Figure 7:
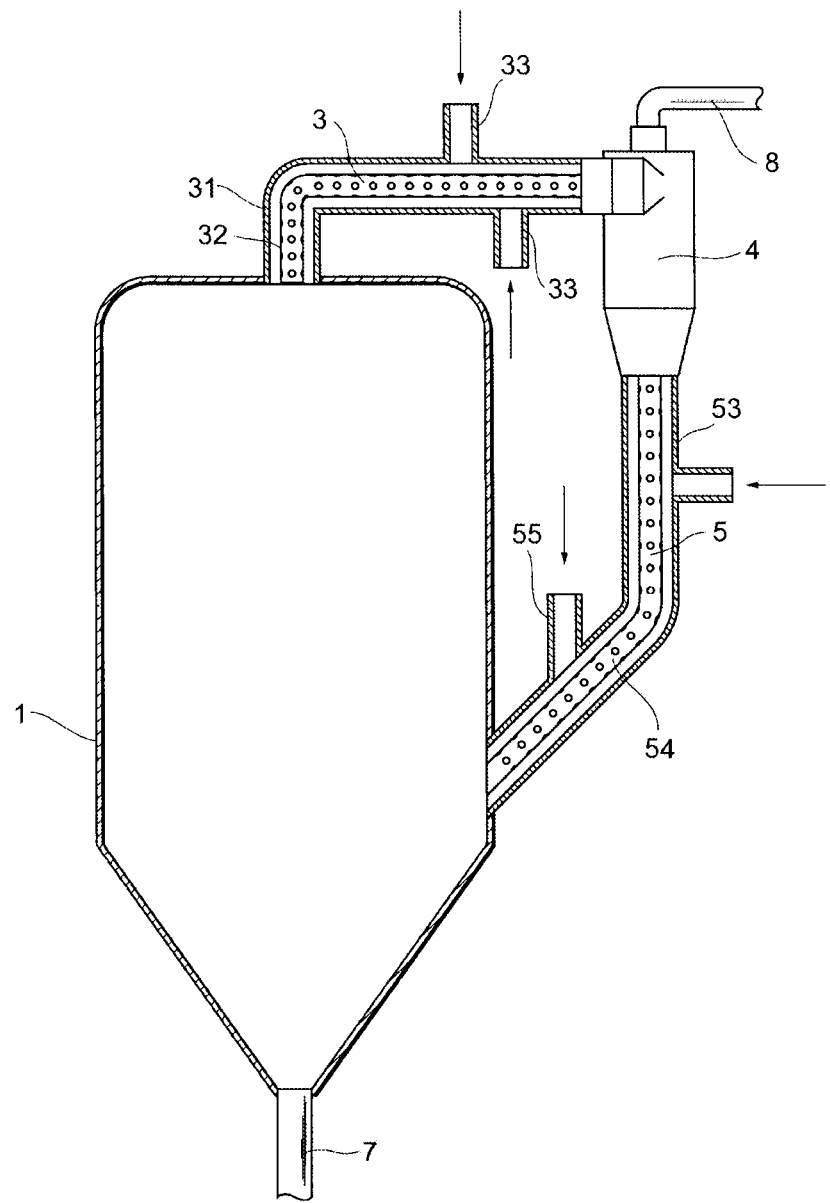
FIG. 7 is a view schematically illustrating an example of an apparatus for removing catalyst surface substances of the embodiment of the present invention.

The apparatus shown in FIG. 7 is nearly the same as the example shown in FIG. 1 except that the outlet pipe 3 and the return pipe 5 each have a double structure; therefore, only the differences between these apparatuses are described. The outlet pipe 3 consists of an outer pipe 31 and an inner pipe 32, and gas is fed between these from a nozzle 33; the return pipe 5 consists of an outer pipe 53 and an inner pipe 54, and gas is fed between these from a nozzle 55. The apparatus shown in FIG. 7 may be used in combination with the apparatus shown in FIG. 6.

From the viewpoint of enhancing the contact efficiency between the gas and the catalyst surface substances, it is preferred that the number of the gas flow passage orifices per the unit mass of the catalyst is larger. The gas flow passage orifices may be provided by directly drilling holes in the wall face of the main body in which the catalyst is housed and allowed to be brought into contact with the gas flow; or alternatively, the passage orifices may be provided by arranging piping, pipes or the like inside the main body, and by making holes in the piping, pipes or the like. However, when the gas flows are mutually contacted, the catalyst particles are also mutually contacted, and hence the catalyst particles may be possibly cracked or chipped; therefore, it is preferable to design in such a way that the gas flows do not intersect with each other. From the viewpoint of preventing the cracking of the catalyst particles and the abrasion of the piping or the main body, preferably the gas flows do not directly contact with the pipes, the wall of the main body or the like.

Figure 3:
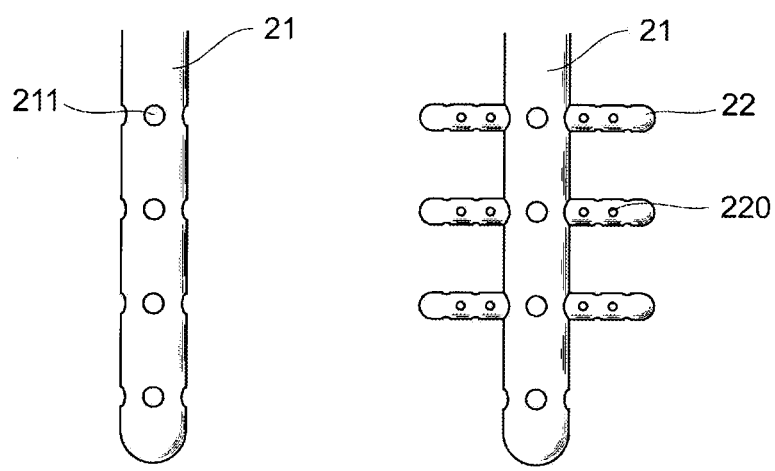
FIG. 3 is a view schematically illustrating an example of a branched chain inside an apparatus for removing catalyst surface substances of the embodiment of the present invention.

The gas flow passage orifice as referred to herein means a hole through which a gas flow enters the interior of the main body under the conditions that a gas flow length in a flow direction of the gas flow is 55 mm or more, and an average flow velocity of the gas flow is 80.0 m/s or more and 500 m/s or less in terms of a linear velocity at 15° C. and at 1 atm; for example, the gas flow passage orifice means the nozzle 210 in FIG. 1, the orifices 211 and 220 in FIG. 3, the orifice 13 in FIG. 6, the inner pipes 32 and 54 in FIG. 7 and the like.

The gas flow length and the linear velocity are correlated with each other to some extent; the gas flow length mainly affects the extent of the region in which the velocity is given to the catalyst, and the linear velocity affects whether or not the gas flow is able to shear the catalyst surface substances in the mentioned region. According to the investigation performed by the present inventors, the removal of the catalyst surface substances involves the action to remove the catalyst surface substances by fluidizing the catalyst so as for the catalyst particles to be brought into contact with each other, and additionally, the action to cut off the catalyst surface substances by the gas flow brought into contact with the catalyst. Accordingly, from this viewpoint, the fluidization of the catalyst by imparting the velocity to the catalyst cannot be said to be essential for the step for removing the catalyst surface substances; however, in the case where the gas flow passage orifices are fixed in the main body, the catalyst present in the vicinity of the gas flow passage orifices moves due to the fluidization of the catalyst, thus the catalyst particles in contact with the gas flow are replaced, consequently the cutting off of the catalyst surface substances in the vicinity of the gas flow passage orifices is effectively performed, and thus, it comes to be possible to remove the catalyst surface substances efficiently not only for the catalyst localized in the vicinity of the gas flow passage orifices, but for the whole catalyst housed inside the main body. In the present embodiment, by setting the gas flow length at 55 mm or more, the number of the catalyst particles fluidized by being imparted the velocity by the gas flow is ensured, and thus the removal of the catalyst surface substances is made to proceed efficiently. By setting the linear velocity at 80 m/s or more, in addition to the removal of the catalyst surface substances due to the mutual contact of the catalyst particles caused by the fluidization of the catalyst, the occurrence of the shear of the catalyst surface substances due to the contact between the gas flow and the catalyst is facilitated to enhance the removal efficiency. On the other hand, by setting the upper limit of the linear velocity not to exceed 500 m/s, the velocity imparted to the catalyst is made to fall within an appropriate range, so as to prevent the cracking and the like of the catalyst particles due to the contact of the catalyst with the main body wall and the mutual contact the catalyst particles.

The size of the gas flow passage orifice is preferably about 0.04 mm to 20 cm in diameter and more preferably about 0.04 mm to 5 cm in diameter; however, the shape of the passage orifice can be optional. The hole diameter of the gas flow passage orifice may be nonuniform. Moreover, it is preferred that the number of the gas flow passage orifices is larger, however, as described above, when the orifices are disposed with the distances between the orifices so as to allow the gas flows to contact with each other, the cracking and the like of the catalyst particles may be caused by the mutually contact of the catalyst particles. Accordingly, in consideration of the following gas flow diameter, gas flow length, gas flow volume and the like derived on the basis of the formulas given by Horio et al. (1) and Yates et al. (2), it is preferable to leave the spaces between the passage orifices so as for the catalyst particles not to contact with each other. In this case, the gas flow length in the flow direction of the gas flow is preferably 10 mm or more from the viewpoints of the contact efficiency and the fluidity of the catalyst, as long as the catalyst particles do not contact with the apparatus, in particular, the main body wall, the pipes and the like. In the present embodiment, the gas flow length can be calculated by using the formula of Yates et al. and the gas flow diameter can be calculated by using the formula of Horio et al.

In the present embodiment, the following symbols are used for the gas flow length: hj: the gas flow length [m], dor: orifice diameter [m], dp: catalyst particle diameter [m], uor: orifice flow rate [m/s], μ: gas viscosity [kg·m/sec], ρg: gas density [kg/m$^3$], ρp: catalyst particle density [kg/m$^3$] and g: gravitational acceleration [m/s$^2$]; with these symbols, the gas flow length is represented by the following formula (in the formula, the symbol "^" means power):

$$hj/dor = 21.2 \cdot (uor^2/(g \cdot dp))^{0.37} \cdot (dor \cdot uor \cdot \rho g/\mu)^{0.05} \times (\rho g/\rho p)^{0.68} \cdot (dp/dor)^{0.24}$$

Additionally, the following symbols are used for the gas flow diameter: dj: gas flow diameter [m], fj: 0.02 (constant), Frj=ρg·uor^2/((1−ε mf)·ρp·dp·g), k=(1−sin φr)/(1+sin φr), φr: repose angle of contact (here, approximated as 30°) and lor: pitch [m]; with these symbols, the gas flow diameter is represented by the following formula (in the formula, the symbol "^" means power):

$$(dj/dor) = 1.56 \cdot ((fj \cdot Frj)/(k^{0.5} \cdot \tan \varphi r))^{0.3} \cdot (dor/lor)^{0.2}$$

Here, the "gas viscosity" and the "gas density" are to be calculated from the temperature, pressure and the like at the time of the embodiment with reference to the air composition. The average particle size of the catalyst can be obtained by measuring the particle size distribution in conformity with the JIS R 1629-1997 "Determination of particle size distributions for fine ceramic raw powders by laser diffraction/scattering method," and by averaging on a volumetric basis. More specifically, a fraction of a dried powder is calcinated at 400° C. for 1 hour in the air, the obtained particles are used as the measurement object and the measurement is performed with a laser diffraction/scattering particle size analyzer (LS230, manufactured by Beckman Coulter, Inc.). The repose angle of the catalyst is measured by the injection method. The injection method means a method in which the catalyst is placed in a vessel, the catalyst is heaped on a horizontal plane by free fall, and the angle formed by the powder is measured. In this case, the repose angle value is significantly varied depending on whether or not the catalyst surface substances are attached to the catalyst surface. Here, the calculation is to be performed on the basis of the approximation that the repose angle is 30°.

(1) Horio, M., T. Yamada, and I. Muchi: Preprints of the 14th Fall Meeting of Soc. of Chem. Engrs., Japan, p. 760 (1980).
(2) Yates, J. G., P. N. Rowe and D. J. Cheesman: AIChE J., 30, 890 (1984).

The flow velocity of the gas flow is calculated on the basis of the area of the gas flow passage orifice and the flow rate of the gas; for the purpose of efficiently removing the catalyst surface substances from the catalyst, the average flow velocity of the gas flows discharged from the individual passage orifice is 80 m/s or more and 500 m/s or less and preferably 200 m/s or more and 341 m/s or less in terms of the linear velocity at 15° C. and 1 atm.

Here, the blowoff flow rate Y (m$^3$/h) and the flow velocity u (m/s) of the gas flow can be calculated according to the following calculation formulas, respectively, wherein the following symbols are used: the inner pressure of the nozzle pipe: a (kg/cm$^2$G), the nozzle portion pressure: b (kg/cm$^2$G), and the concerned temperature and pressure of the gas: k (° C.) and p (kPa), respectively, and the area of the gas passage orifice: S (m$^2$). By averaging the obtained linear velocities, the average flow velocity of the gas flow can be obtained.

$$Y = 0.77 \times \sqrt{\frac{2 \times (a-b) \times 98067}{1.29 \times \frac{273.15}{(273.15+k)} \times \frac{(1.033+p)}{1.033}}} \times S \times 3600$$

$$u = Y \times \frac{(1.033+a)}{(1.033+b)} \div S \div 3600$$

The time during which the gas flow is brought into contact with the catalyst is preferably 10 hours or more and 100 hours or less. When the time of the contact is less than 10 hours, the catalyst surface substances tend to remain on the catalyst surface, and when the time of the contact exceeds 100 hours, the catalyst surface tends to be scraped to degrade the production efficiency of the catalyst. The time of the contact between the gas and the catalyst is preferably 15 hours or more and 60 hours or less. For the purpose of enhancing the circulation of the catalyst and more efficiently removing the catalyst surface substances, a mechanism in which the catalyst is conveyed and circulated with a pneumer or the like so as to be brought into contact with the gas flow may be provided, or alternatively the efficiency of the contact with the gas flow may be enhanced by introducing a propeller-like or rod-like rotating member into the main body and by stirring the catalyst by rotating the rotating member.

The catalyst surface substances exfoliated from the catalyst by the apparatus are much smaller than the spherical catalyst particles, therefore the substances flow out together with the flowing gas, and hence can be captured with a filter or the like. However, there is a possibility that the fine catalyst particles are simultaneously captured with the filter, and accordingly it is preferable to enhance the separation efficiency by using a separation device such as a cyclone. A plurality of separation devices such as cyclones may be disposed, or alternatively different separation devices may also be used in combination. In consideration of such a case that a mixture compose of the fine catalyst particles and the catalyst surface substances or the like returns from the cyclone into the main body, the following mechanism may also be provided: a mechanism in which a three-way valve, for example, is disposed in the lower part of the cyclone so as to be able to separately collect the components of such a mixture outside the system. The separated catalyst component is again conveyed into the interior of the main body, and in this case, it is preferable to return the catalyst to such a location where the catalyst is again brought into contact with the gas flow. For example, when the overall gas flow finally goes upward, the catalyst is also considered to go upward along the gas flow, and hence it is preferable to provide a return opening for the separated catalyst at a position lower than the orifices for the gas flow. When the repose angle of the catalyst surface substances is large or when the catalyst surface substances are viscous, the catalyst surface substances possibly adhere to the wall face inside the main body, and moreover, adhere to the pipes to possibly block the pipes, and hence it is preferable to appropriately introduce inside the system a knocker, purge air or the like. Further, for the purpose of removing the catalyst surface substances attached to the pipes, a mechanism to wash the pipes with a liquid such as water, an alcohol or the like may also be provided.

A more preferred aspect of the apparatus for removing a catalyst surface substance in the present embodiment is an apparatus comprising a collection device for collecting the catalyst provided in an upper portion of the main body; and a return device for returning the catalyst, connected to the collection device, wherein the return device is placed so as for a lower end thereof to be brought into contact with the gas flow, and a fraction of the catalyst, brought into contact with the gas flow in the main body is collected by the collection device and returned inside the main body by the return device.

Here, the collection device for collecting the catalyst corresponds to the outlet pipe 3 and the cyclone 4 in FIG. 1 and the return device for returning the catalyst corresponds to the return pipe 5 in FIG. 1.

The collection device is preferably a device for separating the catalyst and the catalyst surface substances from each other by a centrifugal force. Here, the device for separating the catalyst by a centrifugal force corresponds to the above-described cyclone 4.

Further, the apparatus for removing the catalyst surface substance in the present embodiment preferably has a device for capturing the catalyst surface substance removed from the catalyst. Here, the device for capturing the catalyst surface substance corresponds to the above-described filter.

In the present embodiment, the catalyst can be produced, for example, by the following four steps.

(I) Step of obtaining a raw material mixed solution by mixing the raw materials (II) Step of obtaining a catalyst precursor by drying the raw material mixed solution obtained in the step (I)

(III) Step of obtaining a catalyst by calcinating the catalyst precursor obtained in the step (II)

(IV) Step of removing the catalyst surface substances from the catalyst obtained in the step (III)

Hereinafter, the individual steps are described.

(Step I: Raw Material Mixing Step)

The mixing in the present step means the dissolution or dispersion of the raw materials of the catalyst constituting elements in an aqueous solvent. In the production of the catalyst of the present embodiment, metal materials are not particularly limited. When the raw material mixed solution is continuously prepared, the solid components of the raw material mixed solution may adhere, for example, to a mixing tank such as a stirring tank and to the pipe for sending the solution for the drying step. Such solid components possibly cause the troubles such as the obstruction of the pipe when the catalyst is continuously produced, and accordingly it is preferable to clean as needed the inside of the pipe and the tank wall and the like contacting the raw material mixed solution.

(Step II: Drying Step)

In the step (II), the raw material mixed solution obtained in the step (I) is dried by a spray drying method or the like to yield a catalyst precursor. As the spraying method in the spray drying method, a centrifugal technique, a two-fluid nozzle technique or a high pressure nozzle technique can be used; preferable among these is the centrifugal technique. In the centrifugal technique, a distribution plate of a few centimeters in diameter, for example, is revolved at a high speed of a few thousands rpm, and the raw material mixed solution can be sprayed by dropping this solution onto the distribution plate. In this case, the raw material mixed solution may be dropped onto one position on the distribution plate, or alternatively, preferably onto a few separate positions.

As the drying heat source, the air heated by steam, an electric heater or the like can be used. The temperature of the hot air at the dryer inlet is preferably 150 to 250° C. The temperature of the hot air at the dryer outlet is preferably 90° C. or higher and more preferably 90 to 150° C. When the catalyst is continuously produced, it is necessary to perform the operations while appropriately removing the dirt of the dryer main body, the solution sending pipe, the sprayer, the pipe for discharging the catalyst precursor and the like.

(Step III: Calcination Step)

In the present step, the catalyst precursor obtained in the drying step is calcinated to yield the catalyst. The calcination can be performed by using a furnace such as a tunnel furnace, a tube furnace, a rotary furnace or a fluidized calcination furnace. The calcination can be performed repeatedly. The catalyst precursor obtained in the drying step is transferred into the calcination apparatus with a pneumer or the like, when an inert gas such as nitrogen is used in the case where the calcination is performed in the non-presence of oxygen. When gas flow conveyance is performed with a pneumer or the like, a gas-solid separator such as a cyclone is disposed in the calcination apparatus.

When the catalyst precursor is calcinated in a still standing condition, the catalyst precursor is not calcinated uniformly to degrade the performances and offer a cause for the occurrence of the powder adhesion inside the calcination furnace; therefore, in consideration of the productivity as an industrial catalyst, it is preferable to perform the calcination with a rotary kiln or the like. The calcination is usually performed at a number of revolutions of the kiln of a few rpm to a few tens rpm, and the number of revolution may be even 1 rpm or less as long as a non-rotating condition is avoided.

When the catalyst precursor is continuously calcinated, from the viewpoint of stably maintaining the feed rate of the precursor fed to the rotary kiln, a screw feeder or the like can be used. A device such as a screw feeder and a pneumer may be combined, or alternatively the catalyst precursor discharged from the device such as a screw feeder may be fed by being made to fall in a vertical pipe.

When the powder present during calcination adheres to the inner wall of the calcination pipe, the adhering powder is excessively calcinated and the powder passing through without adhering undergoes degraded heat transfer, and thus both degrade the catalyst performances; accordingly it is preferable to exert impact to the kiln main body with a knocker, a hammer or the like. The impact may be exerted with either of a human means or a mechanical means without causing any problem, and preferably the impact is continuously exerted. The end (the portion contacting the calcination pipe) of the knocker or the hammer, made of a metal, can be used.

In the calcination step, for the purpose of obtaining satisfactory performances, the calcination is preferably performed in multiple divided stages such as a pre-calcination, a main calcination and a post-calcination. The main calcination means the calcination stage maintaining the highest temperature in the calcination process, and the pre-calcination means the calcination stage preceding the main calcination. The pre-calcination may be further divided into several stages. The post-calcination means the calcination stage subsequent to the main calcination. The post-calcination may be further divided into several stages. The main calcination is preferably performed at 500 to 800° C. When the pre-calcination, the main calcination and the post-calcination are performed respectively with separate kilns, storage vessels such as hoppers are disposed midway between the kilns and the calcinated products can be conveyed with a pneumer or the like.

Although the atmosphere for the calcination can be the air, when the calcination is performed in the atmosphere substantially free from oxygen for the purpose of maintain the performances, the calcination is preferably performed while an inert gas such as nitrogen is being fed to the calcination apparatus. In this case, a gas-solid separator such as a cyclone is disposed in the gas discharge path to collect the entrained powder that is being calcinated. The collected powder may be returned as it is to the calcination apparatus, or may be collected separately. In the case of a rotary kiln, the collected powder can also be returned to the powder feed section of the kiln.

(Step IV: Step of Removing Catalyst Surface Substances)

The catalyst prepared as described above contains the catalyst surface substances in the vicinity of the surface of the catalyst, and hence it is necessary to remove these substances. The method for removing the catalyst surface substance of the present embodiment is a method in which the catalyst surface substance is removed from the catalyst by bringing a gas flow into contact with the catalyst, the method comprising a step of bringing a gas flow into contact with the catalyst having the catalyst surface substance, wherein a gas flow length in a flow direction of the gas flow is 55 mm or more, and an average flow velocity of the gas flow is 80 m/s or more and 500 m/s or less in terms of a linear velocity at 15° C. and 1 atm.

The method for removing the catalyst surface substance of the present embodiment is preferably combined with a method in which a high-speed gas (gas flow) is made to flow, the gas flow is brought into contact with the catalyst, thus the catalyst is fluidized and the catalyst surface substances on the catalyst surface are simultaneously removed by the gas flow shear, and at the same time the catalyst surface substances are also removed by the mutual contact between the moving catalyst particles. In this case, it does not matter what the type of the gas is; however, dried air or an inert gas such as nitrogen is preferable.

The present inventors have considered that the product between the gas flow volume (V) and the number of the gas passage orifices (K) reflects the total volume of the gas flow which can give the velocity to the catalyst, and have assumed that the product multiplied by the gas flow velocity (u) squared can be used as a substitute for the total energy to be used for removing the catalyst surface substances. While the individual variables are independently being varied, the remaining amount of the catalyst surface substances in the catalyst of a catalyst amount (M) has been measured as a function of time, and the relation between the value obtained by dividing $u^2 \times V \times K$ by the catalyst amount (M) and the time in which a sufficient amount of the catalyst surface substances is removed from the catalyst surface has been examined. Consequently, it has been found that $u^2 \times V \times K/M$ is approximately inversely proportional to the time required for the processing, and it has thus been suggested that $u^2 \times V \times K/M$ is appropriate as an index for the concerned energy (hereinafter, $u^2 \times V \times K/M$ is also referred to as the "converted energy value").

When the catalyst is produced in an industrial scale, in view of the easiness in performing operations, it can be said that it is preferable to design the individual steps so as to each fit in a certain period of time; as for the step for removing the surface substances, the processing time designed so as to complete the operation, for example, within one day facilitates the operation. As described above, the converted energy value is in an approximately inversely proportional relation with the time required for the removal processing, and accordingly, by increasing the converted energy value to some extent, the processing time being in an approximately inversely proportional relation with the converted energy value can be made to fall within a preferable time range. From the viewpoint of making the time of the step for removing the surface substances fall within one day, the present inventors have experimentally investigated the preferable converted energy value, and have found that it is preferable to set $u^2$, V, K and M in such a way that the converted energy value $u^2 \times V \times K/M$ ($m^5/s^2/kg$) for the removal of the catalyst surface substances represented by using the flow velocity u (m/s) of the gas flow, the volume V ($m^3$) formed by the gas flow having passed through the passage orifices, the number K of the passage orifices inside the main body and the mass M (kg) of the catalyst housed inside the main body satisfies the following formula:

$$14 < u^2 \times V \times K/M$$

On the other hand, it has also been found that from the viewpoint of preventing the cracking of the catalyst particles due to the mutual contact of the catalyst particles and/or the contact of the catalyst particles with the main body, it is preferable to set the converted energy value so as to satisfy the following formula:

$$u^2 \times V \times K/M < 100$$

In other words, it has been found that by satisfying the following formula (1):

$$14 < u^2 \times V \times K/M < 100 \quad (1)$$

the processing time of the removal step can be suppressed to fall within a certain range and the cracking of the catalyst particles can be prevented, and hence the catalyst surface substances can be more efficiently removed from the catalyst surface. The preferable value of the converted energy value also depends on the factors associated with the removal apparatus, and is varied depending on the factors such as the shape of the apparatus, the size of the apparatus, the orientations of the nozzles and the contact with the wall of the apparatus. In the case of the apparatus having a size suitable for industrial use, it is more preferable to satisfy the formula $20 < u^2 \times V \times K/M < 90$, and it is furthermore preferable to satisfy the formula $30 < u^2 \times V \times K/M < 80$.

A further investigation of the catalyst amount as the object of the processing, from the viewpoint of the industrial scale production of the catalyst, shows that when the mass M of the catalyst is 1 kg or more, it is realistic to set the number K of the passage orifices to be 2 or more in order that the formula $14 < u^2 \times V \times K/M$ may be satisfied under the condition that the average flow velocity of the gas flow is set at 500 m/s or less. Specifically, when the catalyst is processed in a certain amount or more so as to satisfy the formula (1), the number of the passage orifices is generally two or more, and hence the interaction between the gas flows fed from the individual passage orifices occurs. As described above, from the viewpoint of preventing the cracking or chipping of the catalyst particles, it is a preferable aspect that the passage orifices are disposed so as for the gas flows not to intersect or contact with each other; however, even in such a case, the effect of a gas flow occurs and the flow of the gas occurs even at a position separated from the passage orifice for the gas flow by a distance of the gas flow length or more. In other words, even when the adjacent passage orifices are disposed so as to be separated from each other by the gas flow length or more, the gas flows fed from the individual passage orifices interact with each other to affect the flow of the catalyst. The flow of the catalyst due to the interaction of the gas flows fed from such two or more passage orifices is an index not to be reflected to the gas flow length and the average velocity of the gas flow, and is an effect not to be obtained in the case where the processing is performed with a single passage orifice. Accordingly, when the formula $14 < u^2 \times V \times K/M < 100$ is satisfied and the formula $K \geq 2$ holds, owing to the flow of the catalyst due to the interaction of the gas flows fed from the two or more passage orifices, the catalyst surface substances can be removed even more efficiently.

When two or more passage orifices are provided, the spacing between the passage orifices is preferably equal to or larger than the gas flow diameter from the viewpoint of preventing the cracking of the catalyst particles, and is preferably two times or less the gas flow diameter from the viewpoint of increasing the fluidity of the catalyst by the gas flow interaction caused by the gas flows. Preferably, during the operation of the apparatus, the catalyst is subjected, as needed, to sampling to estimate the amount of the catalyst surface substances. The sampling can be performed from the catalyst collection line provided in the main body of the apparatus. Alternatively, a sampling line may be set up at another position. In general, when the converted energy value is large, the removal rate of the catalyst surface substances from the catalyst surface is fast, but the cracking of the catalyst particles tends to occur to a larger extent; when the converted energy value is small, the cracking of the catalyst particles tends to occur to a less extent, but the removal rate is slow.

Here, the volume V (m³) formed by the gas flow having passed through the passage orifice can be calculated from the following formula on the assumption that the gas flow having passed through the passage orifice is approximately a circular column:

Volume $V$=gas flow radius×gas flow radius×π×gas flow length

The method for producing an unsaturated acid or an unsaturated nitrile of the present embodiment is a production method wherein the catalyst surface substances are removed from the catalyst by using the above-described apparatus, the catalyst from which the catalyst surface substances have been removed is used, and an alkane and/or an alkene is subjected to an oxidation reaction or an ammoxidation reaction to produce a corresponding unsaturated acid or unsaturated nitrile. As the method for the oxidation reaction or the ammoxidation reaction, a generally known vapor phase contact oxidation reaction or a generally known vapor phase contact ammoxidation reaction or the like can be adopted.

EXAMPLES

Hereinafter, the apparatus and the method for removing the catalyst surface substance of the present embodiment are described by using the examples of the preparation of the catalyst and the examples of the production of acrylonitrile based on the vapor phase contact ammoxidation reaction of propane; however, the present embodiment is not limited to these examples as long as the present embodiment does not deviates from the gist of the present embodiment.

The achievement of the ammoxidation reaction of propane was estimated on the basis of the analysis of the reaction gas and by using as an index the acrylonitrile yield (AN yield) defined by the following formula:

Yield of acrylonitrile (%)=Number of moles of produced acrylonitrile/number of moles of supplied propane×100

The analysis of the reaction gas was performed as follows.
Here, the number of moles of the produced acrylonitrile was measured with a thermoconductivity detector-type gas chromatograph GC-2014 AT manufactured by Shimadzu Corp.

(Preparation of Niobium Mixed Solution)

A niobium mixed solution was prepared by the following method.

In 255.2 kg of water, 35.2 kg of niobic acid having a content of 80 mass % in terms of $Nb_2O_5$ and 134.4 kg of oxalic acid dihydrate ($H_2C_2O_4.2H_2O$) were mixed. The charged molar ratio of oxalic acid/niobium was 5.03 and the charged niobium concentration was 0.50 (mol-Nb/kg-solution).

The solution was heated at 95° C. for 1 hour under stirring to prepare a mixed solution containing niobium dissolved therein. The mixed solution was allowed to stand still and ice-cooled, and then the solid content was filtered out by suction filtration to prepare a homogeneous niobium mixed solution. This operation was repeated several times and the filtrates were collected and mixed. The niobium mixed solution thus obtained was found to have a molar ratio of oxalic acid/niobium of 2.52 on the basis of the following analysis.

In a crucible, 10 g of the niobium mixed solution weighed out accurately was placed, the solution was dried overnight at 95° C. and heat treated at 600° C. for 1 hour to yield 0.8228 g of $Nb_2O_5$. From this result, the niobium concentration was found to be 0.618 (mol-Nb/kg-solution). In a 300-mL glass beaker, 3 g of the niobium mixed solution weighed out accurately was placed, 200 mL of hot water at about 80° C. was added to the beaker, and successively 10 mL of 1:1 sulfuric acid was added to the beaker. The obtained mixed solution was titrated with a ¼N $KMnO_4$ solution under stirring while the mixed solution was being maintained on a hot stirrer at a solution temperature of 70° C. The point where the faint light pink color due to $KMnO_4$ was maintained for about 30 seconds or more was taken as the end point. The concentration of oxalic acid was calculated from the titrated amount according to the following formula and consequently found to be 1.558 (mol-oxalic acid/kg).

$$2KMnO_4+3H_2SO_4+5H_2C_2O_4 \rightarrow K_2SO_4+2MnSO_4+10CO_2+8H_2O$$

The obtained niobium mixed solution was used as the niobium mixed solution (BO) for the following catalyst preparation.

(Preparation of Catalyst)

The oxide catalyst having the charged composition formula 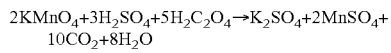 $Mo_1V_{0.21}Nb_{0.09}Sb_{0.25}Ce_{0.005}O_n/45.0$ wt %-$SiO_2$ was produced as follows.

To 38.0 kg of water, 9.2 kg of ammonium heptamolybdate [$(NH_4)_6Mo_7O_{24}\cdot4H_2O$], 12.7 kg of ammonium metavanadate [$NH_4VO_3$], 19.0 kg of diantimony trioxide [$Sb_2O_3$] and 1.15 kg of cerium nitrate hexahydrate [$Ce(NO_3)_3\cdot6H_2O$] were added, heated at 90° C. under stirring for 2 hours and 30 minutes to yield the mixed solution A.

To 75.5 kg of the niobium mixed solution (BO), 10.6 kg of an aqueous hydrogen peroxide solution containing 30 wt % of $H_2O_2$ was added and stirred at room temperature for 10 minutes to prepare the mixed solution B. The obtained mixed solution A was cooled down to 70° C., and then 18.4 kg of a silica sol containing 29.3 wt % of $SiO_2$ was added to the mixed solution A and further 2.2 kg of an aqueous hydrogen peroxide solution containing 30 wt % of $H_2O_2$ was added to the mixed solution, and the obtained mixed solution was continuously stirred at 50° C. for 1 hour. Next, to this mixed solution, the mixed solution B was added. To the thus obtained mixed solution, 50.4 kg of an aqueous dispersion prepared by dispersing 3.6 kg of fumed silica having an average primary particle size of 12 nm was added to prepare the raw material mixed solution.

The obtained raw material mixed solution was fed to a centrifugal spray dryer so as to be dried to yield a dried microspherical powder. The inlet temperature of the dryer was 210° C. and the outlet temperature of the dryer was 120° C.

The above-described operations were repeated, the dried powders were collected and thus about 3 t of the catalyst precursor having the catalyst surface substances attached thereto was obtained.

The obtained catalyst precursor was made to flow, at a flow rate of 20 kg/hr, through a SUS cylindrical calcination pipe of 500 mm in inner diameter, 3500 mm in length and 20 mm in wall thickness, having seven sheetings of 150 mm in height disposed so as to equally divide, into eight divisions, the length of the heating furnace portion; the pre-calcination was performed in a flow of nitrogen gas having a flow rate of 600 N liter/min, while the calcination pipe was being rotated at 5 rpm, and the temperature of the heating furnace was regulated in such a way that the temperature profile was such that the temperature was increased to 360° C. over about 4 hours and the temperature was maintained at 360° C. for 3 hours; thus the pre-calcinated powder was obtained. The pre-calcinated powder was made to flow, at a flow rate of 15 kg/hr, through another SUS cylindrical calcination pipe of 500 mm in inner diameter, 3500 mm in length and 20 mm in wall thickness, having seven sheetings of 150 mm in height disposed so as to equally divide, into eight divisions, the length of the heating furnace portion, while the calcination pipe was being rotated at 5 rpm. In this case, while the powder introduction section (the portion not covered with the heating furnace) of the calcination pipe was being hit at a rate of one hit per 5 seconds, in the direction perpendicular to the rotation axis, from the height of 250 mm from the upper portion of the calcination pipe, with a hammering device equipped with a hammer of 14 kg in mass, having a SUS hitting portion end, the main calcination was performed in a flow of nitrogen gas having a flow rate of 500 N liter/min, by regulating the temperature of the heating furnace in such a way that the temperature profile was such that the temperature was increased to 645° C. at a rate of 2° C./min, and the calcination was performed at 645° C. for 2 hours, and then the temperature was decreased at a rate of 1° C./min; thus the oxide catalyst was obtained. The catalyst surface substances were found to be attached to the surface of the catalyst thus obtained. During the main calcination, the decrease of the calcination temperature was not found to occur and the oxide catalyst was able to be obtained at a stable rate.

Hereinafter, the examples of the removal step of removing the catalyst surface substances attached to the catalyst obtained as described above are described by using the drawings.

The converted energy value per the unit mass of the catalyst ($m^5/s^2/kg$) in each of the following examples was calculated by using the flow velocity u (m/s) of the gas flow at the passage orifice, the volume V ($m^3$) formed by the gas flow having passed through the passage orifice, the number K of the passage orifices inside the main body, and the mass M (kg) of the catalyst housed inside the main body, and on the basis of the following formula (2):

$$u^2 \times V \times K/M \qquad (2)$$

Here, the flow velocity u (m/s) of the gas flow at the passage orifice and the volume V ($m^3$) formed by the gas flow having passed through the passage orifice were measured as described above. In performing the various calculations, the catalyst particle density ($kg/m^3$) is a value obtained by dividing the mass of a catalyst particle by the volume of a catalyst particle, and unless otherwise specified, calculations were performed in the present examples and the comparative examples with the catalyst particle density defined to be 2500 $g/m^3$.

The proportion of the catalyst surface substances remaining in the crystal was calculated with the following formula:

$$WR = [W0 \sim 20/W0] \times 100 (\%)$$

wherein

WR: Proportion of the catalyst surface substances remaining in the crystal (mass %)

W0: Initially fed amount (=50 g)

W0~20: Mass (g) of the catalyst surface substances removed from the catalyst and captured on a paper filter in an elapsed time of 20 hours from the start of the removal and capturing.

Here, the mass of the catalyst surface substances removed from the catalyst and captured on the paper filter was measured as follows. Specifically, 50 g of the catalyst was weighed out accurately, and was placed in a vertical tube, of 41.6 mm in inner diameter and 70 cm in length, in which the lower end was covered with a perforated disc having three holes of 0.40 mm (1/64 inch) in diameter and the upper end was closed with a paper filter; air was made to flow through the tube from the bottom of the tube at a rate of 380 L/h for 20 hours. The catalyst surface substances exfoliated from the catalyst were captured on the paper filter, and the mass of the catalyst surface substances captured on the paper filter was measured.

The amount of the catalyst processed per unit time represents the mass of the catalyst processed per 1 hour in such a way that the catalyst surface substances is removed to the proportion of the catalyst surface substances in relation to the mass of the whole catalyst reaches 0.8 mass % or less.

Example 1

In an apparatus as shown in FIG. 1, 2500 kg of the catalyst having the catalyst surface substances attached to the catalyst surface was placed, and the operation was performed for 20 hours under the conditions regulated in such a way that the converted energy value per the unit mass of the catalyst ($m^5/s^2/kg$) at 15° C. and at 1 atm was 25. In this case, the gas flow length in the flowing direction of the gas flow was 309 mm, the average linear velocity of the gas flow was 332 m/s, and the number K of the gas passage orifices was 350. Consequently, the mass of the catalyst surface substances collected outside the removal apparatus was 200 kg (8 mass %). The proportion of the catalyst surface substances remaining in the obtained catalyst was 0.4 mass %. The amount of the catalyst processed per unit time was 250 kg/h. The sampling of the catalyst was performed after 5 hours, 10 hours and 15 hours from the start of the operation of the apparatus, and the thus obtained proportions of the catalyst surface substances remaining in the catalyst were found to be 50%, 22% and 6.0%, respectively.

(Ammoxidation Reaction of Propane)

In a vycor glass fluidized bed reactor tube of 25 mm in inner diameter, 40 g of the catalyst prepared in Example 1 was charged, a mixed gas composed of propane, ammonia, oxygen and helium in a molar ratio of 1:1:3:18 was fed with a contact time of 2.8 (sec·g/cc) at a reaction temperature of 440° C. and at a reaction pressure set at normal pressure. Consequently, the AN yield was 54.0%.

Example 2

In an apparatus as shown in FIG. 1, 2000 kg of the catalyst having the catalyst surface substances attached thereto was placed, and the operation was performed for 40 hours under the conditions regulated in such a way that the converted energy value per the unit mass of the catalyst ($m^5/s^2/kg$) at 15° C. and at 1 atm was 15. In this case, the gas flow length in the flowing direction of the gas flow was 267 mm, the average linear velocity of the gas flow was 276 m/s, and the number K of the gas passage orifices was 350. Consequently, the mass of the catalyst surface substances collected outside the removal apparatus was 190 kg (9.5 mass %). The proportion of the catalyst surface substances remaining in the obtained catalyst was 0.2 mass %. The amount of the catalyst processed per unit time was 100 kg/h.

Example 3

In an apparatus as shown in FIG. 1, 1400 kg of the catalyst having the catalyst surface substances attached thereto was placed, and the operation was performed for 15 hours under the conditions regulated in such a way that the converted energy value per the unit mass of the catalyst ($m^5/s^2/kg$) at 15° C. and at 1 atm was 40. In this case, the gas flow length in the flowing direction of the gas flow was 302 mm, the average linear velocity of the gas flow was 323 m/s, and the number K of the gas passage orifices was 350. Consequently, the mass of the catalyst surface substances collected outside the removal apparatus was 125 kg (8.9 mass %). The proportion of the catalyst surface substances remaining in the obtained catalyst was 0.2 mass %. The amount of the catalyst processed per unit time was 93 kg/h.

Example 4

In an apparatus as shown in FIG. 1, 1800 kg of the catalyst having the catalyst surface substances attached thereto was placed, and the operation was performed for 5 hours under the conditions regulated in such a way that the converted energy value per the unit mass of the catalyst ($m^5/s^2/kg$) at 15° C. and at 1 atm was 90. In this case, the gas flow length in the flowing direction of the gas flow was 390 mm, the average linear velocity of the gas flow was 341 m/s, and the number K of the gas passage orifices was 350. Consequently, the mass of the catalyst surface substances collected outside the removal apparatus was 140 kg (7.8 massa). The proportion of the catalyst surface substances remaining in the obtained catalyst was 0.6 mass %. The amount of the catalyst processed per unit time was 360 kg/h.

Example 5

In an apparatus as shown in FIG. 1, 1800 kg of the catalyst having the catalyst surface substances attached thereto was placed, and the operation was performed for 20 hours under the conditions regulated in such a way that the converted energy value per the unit mass of the catalyst ($m^5/s^2/kg$) at 15° C. and at 1 atm was 25. In this case, the gas flow length in the flowing direction of the gas flow was 206 mm, the average linear velocity of the gas flow was 196 m/s, and the number K of the gas passage orifices was 2000. Consequently, the mass of the catalyst surface substances collected outside the removal apparatus was 160 kg (8.9 mass %). The proportion of the catalyst surface substances remaining in the obtained catalyst was 0.3 mass %. The amount of the catalyst processed per unit time was 90 kg/h.

Example 6

In an apparatus as shown in FIG. 1, 1800 kg of the catalyst having the catalyst surface substances attached thereto was placed, and the operation was performed for 20 hours under the conditions regulated in such a way that the converted energy value per the unit mass of the catalyst ($m^5/s^2/kg$) at 15° C. and at 1 atm was 25. In this case, the gas flow length in the flowing direction of the gas flow was 390 mm, the average linear velocity of the gas flow was 335 m/s, and the number K of the gas passage orifices was 100. Consequently, the mass of the catalyst surface substances collected outside the removal apparatus was 130 kg (7.2 mass %). The proportion of the catalyst surface substances remaining in the obtained catalyst was 0.8 mass %. The amount of the catalyst processed per unit time was 90 kg/h.

Example 7

In an apparatus as shown in FIG. 1, 100 kg of the catalyst having the catalyst surface substances attached thereto was placed, and the operation was performed for 20 hours under the conditions regulated in such a way that the converted energy value per the unit mass of the catalyst ($m^5/s^2/kg$) at 15° C. and at 1 atm was 27. In this case, the gas flow length in the flowing direction of the gas flow was 166 mm, the average linear velocity of the gas flow was 230 m/s, and the number K of the gas passage orifices was 250. Consequently, the mass of the catalyst surface substances collected outside the removal apparatus was 8 kg (8.0 mass %). The proportion of the catalyst surface substances remaining in the obtained catalyst was 0.4 mass %. The amount of the catalyst processed per unit time was 20 kg/h.

Example 8

In a vertical tube (inner diameter: 41.6 mm, length: 70 cm) in which the lower end was covered with a perforated disc having three holes of 0.40 mm in diameter and the upper end was closed with a paper filter, 50.0 g of the catalyst weighed out accurately was placed, and the operation was started under the conditions regulated in such a way that the gas flow length in the flowing direction of the gas flow formed by the air entering from each of the holes was 55 mm, the average linear velocity of the gas flow was 327 m/s, and the converted energy value per the unit mass of the catalyst ($m^5/s^2/kg$) at 15° C. and at 1 atm was 25; at an elapsed time of 12 hours, the catalyst was collected. The proportion of the catalyst surface substances remaining in the obtained catalyst was 0.5 mass %. The amount of the catalyst processed per unit time was 4.2 g/h.

Example 9

In an apparatus as shown in FIG. 1, 60 kg of the catalyst having the catalyst surface substances attached thereto was placed, and the operation was performed for 27 hours under the conditions regulated in such a way that the converted energy value per the unit mass of the catalyst ($m^5/s^2/kg$) at 15° C. and at 1 atm was 9. In this case, the gas flow length in the flowing direction of the gas flow was 63 mm, the average linear velocity of the gas flow was 104 m/s, and the number K of the gas passage orifices was 4000. Consequently, the mass of the catalyst surface substances collected outside the removal apparatus was 4.8 kg (8.0 mass %). The proportion of the catalyst surface substances remaining in the obtained catalyst was 0.5 mass %. The amount of the catalyst processed per unit time was 2.2 kg/h.

Example 10

In an apparatus as shown in FIG. 1, 500 kg of the catalyst having the catalyst surface substances attached thereto was placed, and the operation was performed for 22 hours under the conditions regulated in such a way that the converted energy value per the unit mass of the catalyst ($m^5/s^2/kg$) at 15° C. and at 1 atm was 18. In this case, the gas flow length in the flowing direction of the gas flow was 189 mm, the average linear velocity of the gas flow was 340 m/s, and the number K of the gas passage orifices was 350. Consequently, the mass of the catalyst surface substances collected outside the removal apparatus was 38 kg (7.6 mass %). The proportion of the catalyst surface substances remaining in the obtained catalyst was 0.5 mass %. The amount of the catalyst processed per unit time was 23 kg/h.

Example 11

In an apparatus as shown in FIG. 1, 1000 kg of the catalyst having the catalyst surface substances attached thereto was placed, and the operation was performed for 22 hours under the conditions regulated in such a way that the converted energy value per the unit mass of the catalyst ($m^5/s^2/kg$) at 15° C. and at 1 atm was 26. In this case, the gas flow length in the flowing direction of the gas flow was 300 mm, the average linear velocity of the gas flow was 130 m/s, and the number K of the gas passage orifices was 350. Consequently, the mass of the catalyst surface substances collected outside the removal apparatus was 80 kg (8.0 mass %). The proportion of the catalyst surface substances remaining in the obtained catalyst was 0.4 mass %. The amount of the catalyst processed per unit time was 45 kg/h.

Comparative Example 1

In an apparatus as shown in FIG. 1, 1800 kg of the catalyst having the catalyst surface substances attached thereto was placed, and the operation was performed for 20 hours under the conditions regulated in such a way that the converted energy value per the unit mass of the catalyst ($m^5/s^2/kg$) at 15° C. and at 1 atm was 0.05. In this case, the number K of the gas passage orifices was 250, the gas flow length in the flowing direction of the gas flow was 84 mm, and the average linear velocity of the gas flow was 70 m/s. Consequently, the mass of the removed and collected catalyst surface substances was 45 kg (2.5 mass %). The proportion of the catalyst surface substances remaining in the obtained catalyst was 5.3 mass %.

Comparative Example 2

In a vertical tube (inner diameter: 41.6 mm, length: 70 cm) in which the lower end was covered with a perforated disc having three holes of 0.20 mm in diameter and the upper end was closed with a paper filter, 50.0 g of the catalyst weighed out accurately was placed, and the operation was started under the conditions regulated in such a way that the gas flow length in the flowing direction of the gas flow formed by the air entering from each of the holes was 33 mm, the average linear velocity of the gas flow was 340 m/s, and the converted energy and at 1 atm was 3; at an elapsed time of 40 hours, the catalyst was collected. The proportion of the catalyst surface substances remaining in the obtained catalyst was 2.5 mass %.

Comparative Example 3

In an apparatus as shown in FIG. 1, 300 kg of the catalyst having the catalyst surface substances attached thereto was placed, and the operation was performed for 20 hours under the conditions regulated in such a way that the converted energy value per the unit mass of the catalyst ($m^5/s^2/kg$) at 15° C. and at 1 atm was 16. In this case, the number K of the gas passage orifices was 100, the gas flow length in the flowing direction of the gas flow was 285 mm, and the average linear velocity of the gas flow was 73 m/s. Consequently, the mass of the catalyst surface substances collected outside the removal apparatus was 17 kg (5.8 mass %). The proportion of the catalyst surface substances remaining in the obtained catalyst was 2.1 mass %.

Comparative Example 4

In a vertical tube (inner diameter: 41.6 mm, length: 70 cm) in which the lower end was covered with a perforated disc having three holes of 0.40 mm in diameter and the upper end was closed with a paper filter, 50.0 g of the catalyst weighed out accurately was placed, and the operation was started under the conditions regulated in such a way that the gas flow length in the flowing direction of the gas flow formed by the air entering from each of the holes was 49 mm, the average linear velocity of the gas flow was 280 m/s, and the converted energy value per the unit mass of the catalyst ($m^5/s^2/kg$) at 15° C. and at 1 atm was 13; at an elapsed time of 12 hours, the catalyst was collected. The proportion of the catalyst surface substances remaining in the obtained catalyst was 1.5 mass %.

Comparative Example 5

In a vertical tube (inner diameter: 41.6 mm, length: 70 cm) in which the lower end was covered with a perforated disc having seven holes of 0.76 mm in diameter and the upper end was closed with a paper filter, 50.0 g of the catalyst weighed out accurately was placed, and the operation was started under the conditions regulated in such a way that the gas flow length in the flowing direction of the gas flow formed by the air entering from each of the holes was 37 mm, the average linear velocity of the gas flow was 102 m/s, and the converted energy value per the unit mass of the catalyst ($m^5/s^2/kg$) at 15° C. and at 1 atm was 6; at an elapsed time of 12 hours, the catalyst was collected. The proportion of the catalyst surface substances remaining in the obtained catalyst was 4.0 mass %.

Comparative Example 6

In an apparatus as shown in FIG. 1, 1000 kg of the catalyst having the catalyst surface substances attached thereto was placed, and the operation was performed for 40 hours under the conditions regulated in such a way that the converted energy value per the unit mass of the catalyst ($m^5/s^2/kg$) at 15° C. and at 1 atm was 0.2. In this case, the number K of the gas passage orifices was 2000, the gas flow length in the flowing direction of the gas flow was 45 mm, and the average linear velocity of the gas flow was 300 m/s. Consequently, the mass of the catalyst surface substances collected outside the removal apparatus was 30 kg (3.0 mass %). The proportion of the catalyst surface substances remaining in the obtained catalyst was 5.0 mass %.

The present application is based on Japanese Patent Application (Japanese Patent Application No. 2010-105511) filed at Japan Patent Office on Apr. 30, 2010, and the contents thereof are incorporated herein by reference.

INDUSTRIAL APPLICABILITY

According to the present invention, the exuded catalyst surface substances and/or the attached catalyst surface substances on the surface of a catalyst can be efficiently removed from the catalyst.

What is claimed is:

1. An apparatus comprising a main body, the apparatus for removing a catalyst surface substance present on a surface of a catalyst from the catalyst by bringing a gas flow into contact with the catalyst housed inside the main body,
wherein a gas flow length in a flow direction of the gas flow is 55 mm or more, and an average flow velocity of the gas flow is 80 m/s or more and 500 m/s or less in terms of a linear velocity at 15° C. and 1 atm,
wherein gas flow passage orifices are provided in the main body, the gas flow passage comprising:
a gas introduction pipe having a plurality of branched chains, the branched chains being arranged vertically downward, wherein the plurality of branched chains comprise i) secondary branches comprising a plurality of openings, ii) a plurality of openings, or iii) a plurality of nozzles, and the gas flow passage orifices of i) the plurality of openings of the secondary branches, ii) the plurality of openings, or iii) the plurality of nozzles are configured such that the gas flows discharged from the gas flow passage orifices are ejected in a plurality of directions, wherein a lower part of the main body has a conical lower part, and a lower end of each of the branched chains terminates near a surface of the conical lower part of the main body such that the length of a branched chain is shorter for a branched chain further from the center axis of the main body relative to the length of those branched chains positioned near the center axis of the main body,
wherein a lower end of the main body is opened to be connected to a second gas introduction pipe, and wherein the apparatus further comprises a collection device for collecting the catalyst, placed in an upper portion of the main body, and a return device for returning the catalyst, connected to the collection device, wherein the collection device comprises a separation device for separating the catalyst and the catalyst surface substance from each other by a centrifugal force.

2. The apparatus according to claim 1, wherein the return device is placed so as for a lower end thereof to be brought into contact with the gas flow, and a fraction of the catalyst, brought into contact with the gas flow inside the main body is collected by the collection device and returned inside the main body by the return device.

3. The apparatus according to claim 2, further comprising a device for capturing the catalyst surface substance removed from the catalyst.

4. A production method comprising:
removing catalyst surface substances from a catalyst with the apparatus according to claim 1, and
using the catalyst from which the catalyst surface substances have been removed in an oxidation reaction or an ammoxidation reaction to produce a corresponding unsaturated acid or unsaturated nitrile from an alkane and/or alkene.

5. An apparatus comprising a main body, the apparatus for removing a catalyst surface substance present on a surface of a catalyst from the catalyst by bringing a gas flow into contact with the catalyst housed inside the main body,
wherein a gas flow length in a flow direction of the gas flow is 55 mm or more, and an average flow velocity of the gas flow is 80 m/s or more and 500 m/s or less in terms of a linear velocity at 15° C. and 1 atm,
wherein gas flow passage orifices are provided in the main body, the gas flow passage comprising:
an inner pipe having a plurality of orifices and located inside of an outer pipe, wherein the main body has a double structure consisting of the inner pipe and the outer pipe, wherein the gas flow passage orifices of the inner pipe are configured such that the gas flows discharged from the gas flow passage orifices are ejected in a plurality of directions, wherein a lower end of the inner pipe is opened to be connected to a second gas introduction pipe, and wherein the apparatus further comprises a collection device for collecting the catalyst, placed in an upper portion of the main body, and a return device for returning the catalyst, connected to the collection device, wherein the collection device comprises a separation device for separating the catalyst and the catalyst surface substance from each other by a centrifugal force.

6. The apparatus according to claim 5, wherein the return device is placed so as for a lower end thereof to be brought into contact with the gas flow, and a fraction of the catalyst, brought into contact with the gas flow inside the main body is collected by the collection device and returned inside the main body by the return device.

7. The apparatus according to claim 5, further comprising a device for capturing the catalyst surface substance removed from the catalyst.

8. A production method comprising removing catalyst surface substances from a catalyst with the apparatus according to claim 5, and using the catalyst from which the catalyst surface substances have been removed in an oxidation reaction or an ammoxidation reaction to produce a corresponding unsaturated acid or unsaturated nitrile from an alkane and/or alkene.

* * * * *